United States Patent [19]

Nahas

[11] Patent Number: 4,617,686

[45] Date of Patent: Oct. 21, 1986

[54] PROTECTIVE EYEWEAR

[76] Inventor: Arthur G. Nahas, 593 Shore Rd., Somers Point, N.J. 08244

[21] Appl. No.: 593,732

[22] Filed: Mar. 27, 1984

[51] Int. Cl.⁴ .............................................. A61F 9/02
[52] U.S. Cl. ...................................... 2/433; 2/442; 2/447; 2/9
[58] Field of Search ................... 2/431, 433, 439, 441, 2/443, 442, 446, 447, 448, 452, 426, 9

[56] References Cited

U.S. PATENT DOCUMENTS

| | | | |
|---|---|---|---|
| 1,105,630 | 8/1914 | Donnelly . | |
| 1,781,067 | 11/1930 | Micheli . | |
| 1,793,785 | 2/1931 | Dunlap . | |
| 1,959,915 | 5/1934 | Guthrie | 88/41 |
| 2,114,658 | 4/1938 | Noffsinger | 2/12 |
| 2,212,945 | 8/1940 | Lehrfeld | 2/14 |
| 2,427,918 | 9/1947 | Malcom et al. | 2/441 |
| 2,615,163 | 10/1952 | Ring | 2/431 |
| 3,039,110 | 6/1962 | De Vries | 2/433 |
| 3,530,506 | 9/1970 | Hoffmaster | 2/431 |
| 3,952,331 | 4/1976 | Melville | 2/431 |
| 4,168,542 | 9/1979 | Small | 2/9 |
| 4,173,795 | 11/1979 | Lundin et al. | 2/9 X |
| 4,229,837 | 10/1980 | Solari | 2/431 |
| 4,367,561 | 1/1983 | Solari | 2/439 |
| 4,494,251 | 1/1985 | Ainsworth et al. | 2/443 X |

FOREIGN PATENT DOCUMENTS 0864939 2/1941 France ................................... 2/433

OTHER PUBLICATIONS

WO82/02255, Mrcoczkowski, 12-1981.

Primary Examiner—Peter Nerbun
Attorney, Agent, or Firm—Benasutti and Murray

[57] ABSTRACT

Protective eyewear, to be worn while engaging in sporting activities, such as racquetball, squash, etc., includes frame portions each having an upper segment and a lower segment defining a viewing aperture. The upper segment is upwardly inclined from horizontal by a predetermined amount to form an apex portion which outwardly extends from the facial region of the wearer and the lower segment is downwardly inclined from horizontal by a predetermined amount to form an apex portion which outwardly extends from the facial region. Filament members vertically extend across each viewing aperture. The filament members have a predetermined diameter and a predetermined spacing therebetween. In an alternate embodiment, the protective eyewear includes replaceable eyepieces.

31 Claims, 5 Drawing Figures

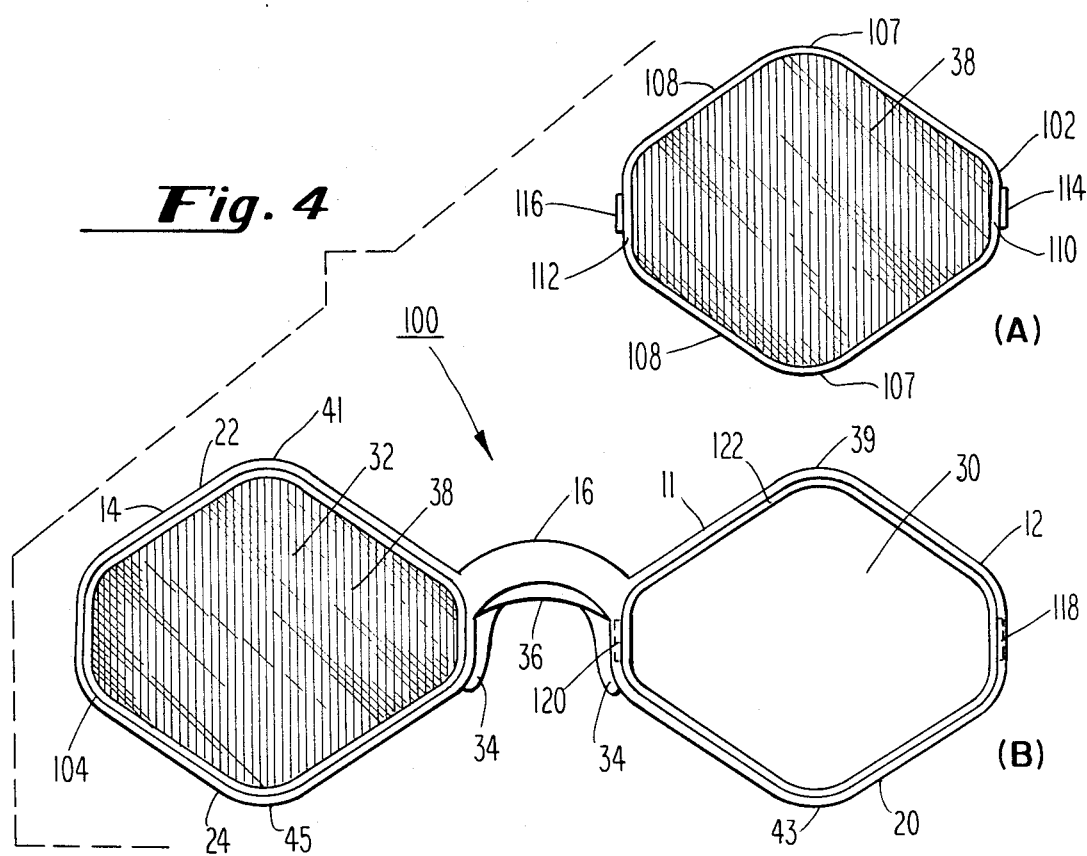
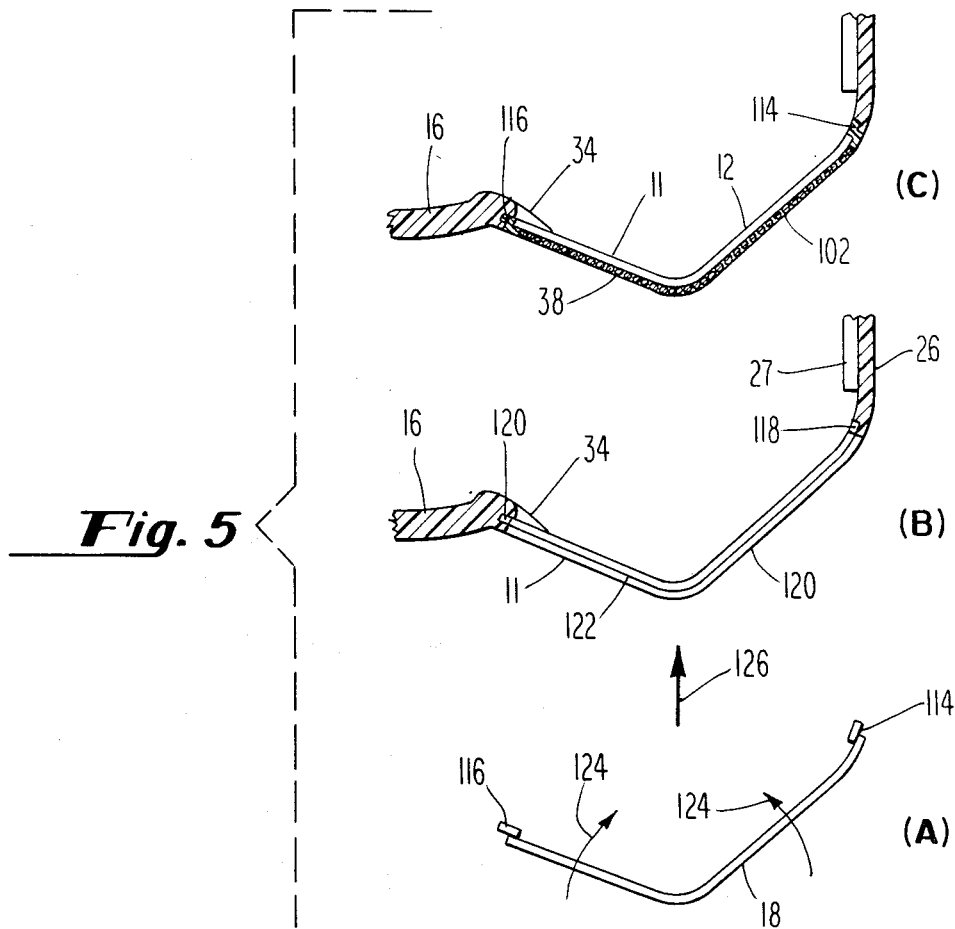

PROTECTIVE EYEWEAR

BACKGROUND OF THE INVENTION

The present invention relates generally to protective eyewear and more particularly to protective eyewear worn while engaging in sporting activities.

Prior art protective goggles include those having transparent lenses for preventing the intrusion of balls, racquets or hands of an opponent into the eye area which could result in severe injury or even loss of vision. Such protective goggles have a tendency to impair vision due to the fact that they become scratched, fogged and/or serve as a collection surface for perspiration or other moisture.

Other types of protective goggles are lensless, but in order to prevent the intrusion of balls or other objects, the openings are relatively narrow thereby restricting vision to a large degree. One attempt to improve upon lensless goggles is disclosed in U.S. Pat. No. 4,229,837. This patent discloses lensless protective eyewear including vertically elongated openings in front of each eye to improve visibility. These openings are relatively restricted in order to prevent the game ball of the sport from penetrating therethrough. Another version includes rod-like members which extend vertically across the central area of view of the wearer and curve outwardly away from the face of the wearer in a protective convex configuration. As shown in FIGS. 10. and 11 of U.S. Pat. No. 4,229,837, this configuration entails the use of members having a relatively thick, rectangular cross-section in order to afford the stated protection. Furthermore, if thinner members are desired, the use of stiff, wirelike elements (see 39 of FIGS. 10a and 10b) constructed of separate metal pieces are disclosed. Although the thick members or metal pieces may retain the protective convex configuration upon impact, they still have a tendency to impair the vision of the wearer which impairment is uncomfortable and burdensome for the participant who wears protective eyewear in fast moving sports such as racquetball and squash. Furthermore, if the metal pieces become bent or broken, or if the rod-like members become broken or marred, the entire goggles will have to be discarded since they are constructed as a single integral piece.

Another type of protective eyewear is disclosed in U.S. Pat. No. 4,367,561. This patent discloses lensless goggles having a construction also aimed at reducing impairment of visibility. These goggles additionally disclose the use of horizontal and vertical projections into the viewing openings for preventing the intrusion of the game ball, racquet or other foreign object, while attempting to minimize obstruction to vision. These projections extend outwardly away from the goggle frames in order to strengthen them against breakage from contact with the game ball, racquet or the like, and to deflect the ball away from the eye of the wearer. Although a purported improvement over the goggles having transparent lenses, the goggles disclosed in U.S. Pat. No. 4,367,561 still hinder vision by use of the outwardly extending projections which, by necessity, have an appreciable thickness and extend into the viewing area in order to prevent the intrusion of the game ball, racquet or the like.

Consequently, it is desirable to provide protective eyewear of relatively lightweight construction, for use in sporting activities such as racquetball, squash and the like, which minimizes impairment to visibility while affording protection and increased comfort.

SUMMARY OF THE INVENTION

It is therefore an object of the present invention to provide protective eyewear for use in sporting activities which afford increased visibility and comfort to the wearer.

It is another object of the present invention to provide protective eyewear having frames which are shaped to diminish the effects of full-face, perpendicular impact of the game ball, racquet or the like.

It is a further object of the present invention to provide protective eyewear having frames which extend outwardly from the eye regions of the viewer in order to create tangential impingement regions to reduce the likelihood of full-face, perpendicular impact and the attendant absorption of maximal kinetic energy imparted by such impact.

It is still another object of the present invention to provide protective eyewear having spaced filaments extending across the viewing area for preventing intrusion of the game ball, racquet or the like.

It is yet another object of the present invention to provide protective eyewear having replaceable eyepieces.

The aforementioned needs are met by the present invention which provides relatively lightweight, comfortable protective eyewear having minimal vision impairment and replaceable eyepieces.

The eyewear of the present invention comprises a frame which includes first and second frame portions having a nose piece connected therebetween. Each frame portion has an upper segment and a lower segment defining a viewing aperture. The upper segment is upwardly inclined from horizontal by a predetermined amount, forming an apex portion which extends outwardly from the facial region of the wearer. The lower segment extends downwardly from horizontal by a predetermined amount, forming an apex portion which extends outwardly from the facial region. At least two filament members extend vertically across each viewing aperture. The filament members have a predetermined spacing therebetween and a predetermined diameter. An alternate embodiment includes removable eyepieces which can be replaced if damaged or broken thereby precluding the need to discard the protective eyewear in its entirety.

BRIEF DESCRIPTION OF THE DRAWINGS

Other objects, features and advantages of the present invention will become more fully apparent from the following detailed description of the preferred embodiment, the appended claims and the accompanying drawing in which:

FIG. 4 is a front elevational view of an alternate preferred embodiment of the protective eyewear having replaceable eyepieces in accordance with the present invention.

FIG. 5 is a partial sectional tip view depicting a replaceable lens and the protective eyewear with and without the replaceable lens inserted therein.

DETAILED DESCRIPTION OF THE PREFERRED EMBODIMENT

Figure 1:
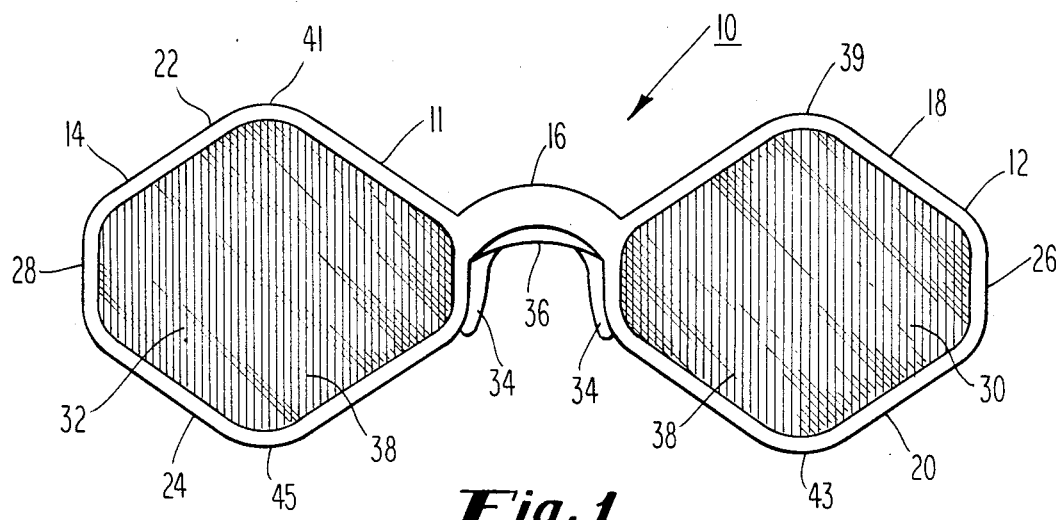
FIG. 1 is a front elevational view of the preferred embodiment of the protective eyewear in accordance with the present invention.

Referring now to FIG. 1, there is shown a preferred embodiment of the protective eyewear of the present invention generally designated 10. The eyewear 10 comprises a one piece frame 11 having first frame portion 12, a second frame portion 14 and a nose piece 16 connected between the first 12 and second 14 frame portions. The first frame portion 12 comprises an upper segment 18 and a lower segment 20. The second frame portion 14 comprises an upper segment 22 and a lower segment 24. The first frame portion 12 includes a temple segment 26. The second frame member 14 also includes a temple segment 28. The upper 18 and the lower 20 segments of the first frame portion 12 define a first viewing aperture 30. The upper segment 22 and lower segment 24 of the second frame portion 14 define a second viewing aperture 32. The one piece frame 11 is preferably constructed of a stiff, transparent or translucent material such as high impact polystyrene or a polycarbonate material such as Lexan, manufactured by the Lexan Products Department of the General Electric Co. The eyewear 10 is constructed such that the first 30 and second 32 viewing apertures are positioned in front of the eyes of the wearer during use.

The nose piece 16 includes nose pads 34 and a nose bridge 36. It is preferred that the nose pads 34 and nose bridge 36 are covered with a soft, resilient material for cushioning blows which are transferred to the nose from the frame portions as well as providing comfort to the wearer. Such a material is preferably polyurethane foam which can be attached to the surfaces of the nose pads 34 and nose bridge 36 by any suitable attachment means such as a contact or pressure sensitive adhesive. It is preferred that each temple segment (26, 28) be lined with a resilient, protective pad 27 (see FIG. 3) for absorbing energy of blows imparted to the temple areas of the head of the wearer. Such a material is preferably polyurethane foam which can be attached to the inner surface of the temple segments 26 and 28 by any suitable attachment means such as a contact or pressure sensitive adhesive. Consequently, the protective eyewear of the present invention preferably contacts the viewer's head only at the temples and the nose area, all of which are lined with resilient material for absorbing blows and enhancing wearing comfort. Although the material for use in the pads 27 or in lining the nose pads 34 and bridge 36 is preferably polyurethane foam, any spongy, resilient, impact cushioning material would be suitable.

Referring again to FIG. 1, it is preferred that the the upper frame segments 18 and 22, of the first 12 and second 14 frame portions respectively, be upwardly inclined at an angle in the range of approximately 30° to 35° with respect to horizontal, thereby forming apex portions 39 and 41 respectively; and the lower frame segments 20 and 24 be inclined downwardly at an angle in the range of approximately 30° to 35° with respect to horizontal thereby forming apex portions 43 and 45 respectively. In addition, as more clearly shown in FIGS. 2 and 3, it is preferred that the apex portions 39 and 41 of the upper 18, 22 frame segments and the apex portions 43 and 45 of the lower 20, 24 frame segments extend outwardly from the forehead and cheek regions of the face in order to increase the likelihood that potentially harmful blows, for example full face blows applied perpendicular to the facial plane, impact the frame tangentially.

Figure 3:
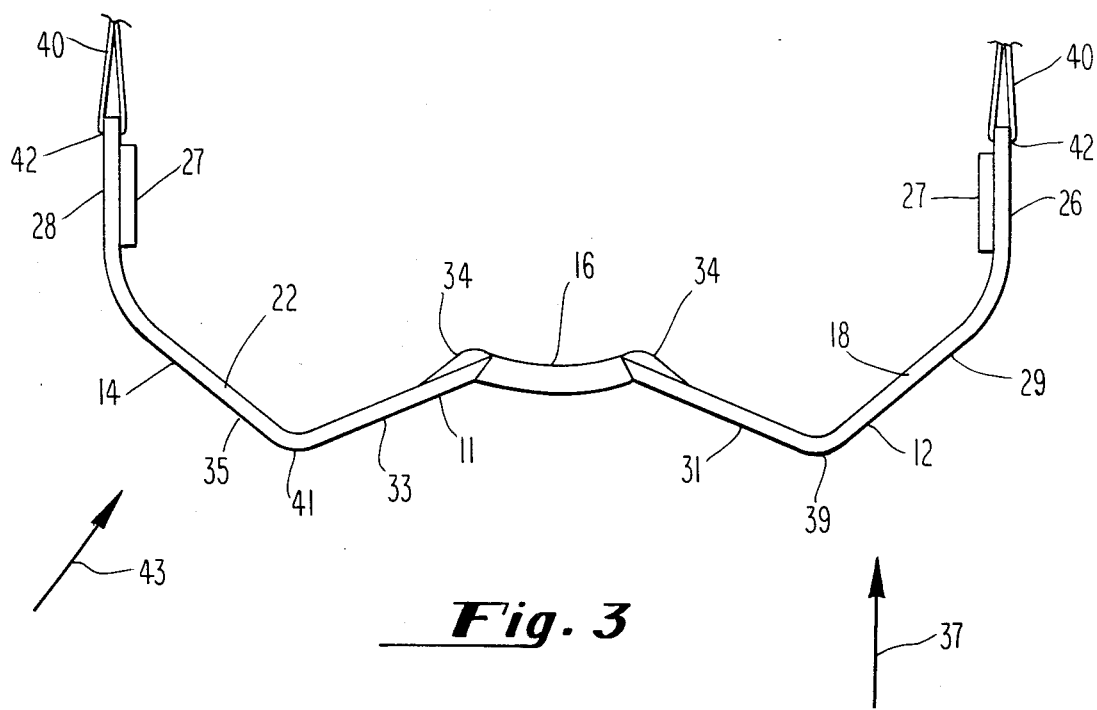
FIG. 3 is a top view of the protective eyewear depicted in FIGS. 1 and 2.

As shown in FIG. 3, a ball which is hit toward the eye in the direction generally indicated by arrow 37 is more likely to tengentially impact the angled portions 29, 31, 33 and 35 of the frame portions 12 and 14 than the apex portions 39 and 41 thereof because of the substantially reduced areas which these apex portions present to the impacting ball as compared to that presented by the angled portions. This improved design reduces the strength requirement of the frame portions since trangential blows do not impart all of their kinetic energy directly to the frames as do perpendicular blows. In addition, this frame construction exhibits increased resistance even to perpendicular blows, for example from the direction generally indicated by arrow 43, due to the relatively short length of angled portion 35 which is required to absorb the kinetic energy imparted by the perpendicular blow, which energy is thereafter transmitted along angled portion 33 and temple member 26.

A plurality of filaments 38 extend vertically across the first 30 and second 32 of eye openings. It is preferred that the filaments be constructed of transparent or translucent high tensile strength polymer material, for example polycarbonate or nylon, having a diameter in the range of approximately 0.2 to 0.6 millimeters. In addition, it is preferred that the spacing between adjacent filaments 38 lie within the range of 0.8 to 4.0 millimeters. Since these filaments extend between the upper (18, 22) frame segments and lower (20, 24) frame segments, the contour of the surface presented by the arrray of vertical filaments will approximate that formed by the upper and lower frame segments. As a result, this surface is also angled thereby minimizing the likelihood of perpendicular impact of full face blows and reducing the strength requirements of the filaments and frames which would otherwise be necessary to absorb the kinetic energy imparted by perpendicular blows.

In addition, the preferred filament diameter, inter-filament spacing and frame configuration, as well as the extensions 50 of the eye openings toward the temple portions 26 and 28 (see FIG. 2), enhance visibility both straight ahead and peripherally. It has been found that utilizing vertically disposed filaments having the ranges of inter-filament spacing and filament diameters set forth in this detailed description, reduces the propensity for the eye to focus upon the filaments. Rather, while engaged in sporting activities such as racquetball, squash, etc., the wearer's eye will tend to focus upon the ball or other relatively distant objects, while ignoring the proximate, evenly spaced filaments which are vertically oriented across the eye openings.

Figure 2:
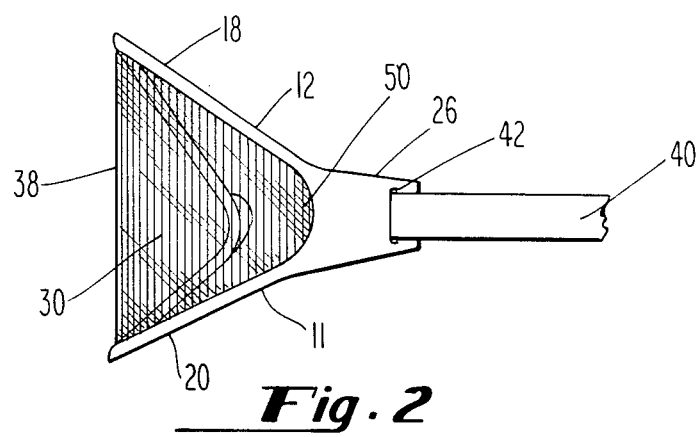
FIG. 2 is a side elevational view of the protective eyewear depicted in FIG. 1.

It is preferred that the frame 11 be molded in one piece using conventional injection or compression molding techniques. The filaments 38 may be either separate elements embedded into the upper and lower frame segments during the molding operation or maybe molded as a solid sheet, or individual filaments, with the frame. The sheet, which preferably has a thickness substantially equal to the preferred diameter of the filaments 38, could then be either etched, by conventional photolithographic etching techniques, or stamped to form the filaments 38. It is preferred that the protective eyewear of the present invention be attached to the wearer's head by means of an elastic band 40 connected to the temple portions 26 and 28 by conventional means, for example through slots 42 as shown in FIG. 2.

An alternate preferred embodiment is depicted in FIGS. 4 and 5. This embodiment of the protective eyewear of the present invention, generally referred to as 100, incorporates replaceable eyepieces 102 and 104 which are removably inserted into the frame 11. Each replaceable eyepiece 102, 104 includes an eyepiece frame 105 comprising an upper segment 106 and a lower segment 108 which are connected by first and second end segments, 110 and 112 respectively. The upper and lower segments, 106 and 108, extend upwardly and outwardly to form apex portions 107 and 109 respectively in the manner previously described with respect to the upper (18, 22) and lower (20, 24) segments of the first and second frame portions, 12 and 14 respectively.

Each replaceable eyepiece 102, 104 also includes a plurality of filaments 38 which vertically extend between the upper 106 and lower 108 segments thereof. The preferred material and diameter of the filaments, as well as the preferred inter-filament spacing, is the same as that previously described with respect to embodiment 10. The preferred material of the eyepiece frame 105 is the same as the preferred material of the frame 11. A first tab 114 extends from the first end segment 110 and a second tab 116 extends from the second end segment 112. The first 114 and second 116 tabs are positioned and dimensioned such that they mate with corresponding first 118 and second 120 receiving slots respectively, which are disposed in opposite ends of each frame portion 12 and 14 of the frame 11 (see FIG. 5C).

The eyepiece frame 105 of the replaceable eyepiece (102, 104) is dimensioned such that it fits within a corresponding frame portion (12, 14) and seats upon a receiving flange 122, which extends around the inner periphery of each frame portion 12 and 14 of the frame 11, when the replaceable eyepiece 102 is inserted therein (see FIG. 5C). It is preferred that the replaceable eyepiece 102 and filaments 38 be molded in one piece. In the alternative, the replaceable eyepiece 102 can be molded with a solid sheet of material extending between the segments of the eyepiece frame 105. This sheet, which preferably has a thickness substantially equal to the preferred diameter of the filaments 38, could then be etched by conventional photolithographic etching techniques or stamped to form the filaments 38.

Referring to FIG. 5, there is shown the preferred method for inserting the replaceable eyepiece 102 into the frame 11. As depicted in FIG. 5A, the ends of the eyepiece 102 are grasped and compressed together in the directions indicated by arrows 124. The eyepiece 102 is then inserted into the frame 11 in the direction indicated by arrow 126 (see FIG. 5B). After the tabs 114 and 116 have been inserted into their respective receiving slots 118 and 120, the eyepiece 102 is released whereupon the eyepiece frame 105 seats upon the mating flange 122 of the receiving frame portion 12, 14 (see FIG. 5C). Note that the orientation of the flange prevents the eyepiece 102 from being driven toward the eye of the wearer by an impacting object. To remove the eyepiece 102, it is grasped and compressed in the directions indicated by arrows 124 until the tabs 114, 116 have been withdrawn from their respective receiving slots 118, 120; whereupon the eyepiece 102 is withdrawn from the frame portion 12, 14.

As can be seen from the above description of the preferred embodiment, the protective eyewear of the present invention affords the wearer ample protection against intrusion by the game ball, racquet or the like while utilizing a unique and relatively lightweight construction which improves visibility and enhances comfort.

It will be understood that various changes in the details, materials and arrangement of parts which have been herein described and illustrated in order to explain the nature of this invention may be made by those skilled in the art within the principle and scope of the invention as expressed in the following claims.

What is claimed is:

1. Protective eyewear adapted for fitting onto a facial region of a wearer's head, said eyewear comprising:
   (a) frame means including first and second frame portions having a nose piece connected therebetween, each frame portion having an upper segment and a lower segment defining a viewing aperture therebetween, said upper segment being upwardly inclined from horizontal by a predetermined amount along straight lines that extend from the side of the frame and from the nose piece to form an apex portion which outwardly extends from said facial region, said lines extending away from the wearer's facial region as they approach the apex portion, and said lower segment being downwardly inclined from horizontal by a predetermined amount to form an apex portion which outwardly extends from said facial region; and
   (b) at least two substantially straight filament members vertically extending under tension cross each said viewing aperture, said filament members having a predetermined diameter and a predetermined spacing therebetween.

2. Protective eyewear in accordance with claim 1 wherein said upper segment is upwardly inclined from horizontal at an angle substantially in the range of from 30° to 35°.

3. Protective eyewear in accordance with claim 2 wherein said lower segment is downwardly inclined from horizontal at an angle substantially in the range of from 30° to 35°.

4. Protective eyewear in accordance with claim 1 wherein the diameter of each of said filament members lies in a range of 0.2 to 0.6 millimeters.

5. Protective eyewear in accordance with claim 4 wherein the spacing between adjacent filament members is within the range of 0.8–4.0 millimeters.

6. Protective eyewear in accordance with claim 1 wherein each of said first and second frame portions includes a temple segment adapted for fitting in close proximity to the temple areas of the facial region of said wearer.

7. Protective eyewear in accordance with claim 6 wherein each temple segment includes means for cushioning blows transmitted from said temple segments to said temple areas.

8. Protective eyewear in accordance with claim 7 wherein said cushioning means comprises a resilient protective pad attached to said temple segment and adapted to contact said temple area.

9. Protective eyewear in accordance with claim 6 wherein said viewing apertures extend into said temple segments.

10. Protective eyewear in accordance with claim 1 wherein said nose piece additionally includes a nose bridge having nose pads at each end thereof.

11. Protective eyewear in accordance with claim 10 wherein said nose bridge and nose pads include means for cushioning blows transmitted from said nose piece to the nose of said wearer.

12. Protective eyewear in accordance with claim 11 wherein said cushioning means comprises a resilient protective liner attached to said nose bridge and nose pads and adapted to contact the nose of said wearer.

13. Protective eyewear in accordance with claim 1 additionally comprising means to secure said frame means to the head of said wearer.

14. Protective eyewear in accordance with claim 13 wherein said securing means comprises an elastic band attached between each of said temple members.

15. Protective eyewear adapted for fitting onto a facial region of a wearer's head, said eyewear comprising:
   (a) frame means including first and second frame portions having a nose piece connected therebetween, each frame portion having an upper segment and a lower segment defining a viewing aperture therebetween, adapted to matingly receive a replaceable eyepiece therein, said upper segment being upwardly inclined from horizontal by a predetermined amount along straight lines that extend from the side of the frame and from the nose piece to form an apex portion which outwardly extends from said facial region, said lines extending away from the wearer's facial region as they approach the apex portion, and said lower segment being downwardly inclined from horizontal by a predetermined amount to form an apex portion which outwardly extends from said facial region; and
   (b) said replaceable eyepiece, adapted for removeable insertion into and mating with the viewing aperture of said frame means, comprising a frame having at least an upper segment and a lower segment and at least two substantially straight filament members vertically extending under tension between said upper and lower eyepiece segments, said filament members having a predetermined diameter and a predetermined spacing therebetween.

16. Protective eyewear in accordance with claim 15 wherein the ends of said upper and lower segments of said eyepiece frame are connected by first and second end segments.

17. Protective eyewear in accordance with claim 16 wherein said first and second end segments each have at least one tab extending therefrom, said tabs being positioned for insertion into corresponding receiving slots disposed in said frame portions and retaining said eyepiece in mating relationship with said frame portion.

18. Protective eyewear in accordance with claim 17 wherein each frame portion includes a flange extending around the inner periphery thereof for maintaining said eyepiece in position within said frame portion.

19. Protective eyewear in accordance with claim 15 wherein said upper segment is upwardly inclined from horizontal at an angle substantially in the range of from 30° to 35°.

20. Protective eyewear in accordance with claim 15 wherein said lower segment is downwardly inclined from horizontal at an angle substantially in the range of from 30° to 35°.

21. Protective eyewear in accordance with claim 15 wherein the diameter of each of said filament members is within a range of approximately 0.2 to 0.6 millimeters.

22. Protective eyewear in accordance with claim 15 wherein the spacing between adjacent filament members is within a range of approximately 0.8 to 4.0 millimeters.

23. Protective eyewear in accordance with claim 15 wherein each of said first and second frame portions includes a temple segment adapted for fitting in close proximity to the temple areas of the facial region of said wearer.

24. Protective eyewear in accordance with claim 23 wherein each temple segment includes means for cushioning blows transmitted from said temple segments to said temple areas.

25. Protective eyewear in accordance with claim 24 wherein said cushioning means comprises a resilient protective pad attached to said temple segment and adapted to contact said temple area.

26. Protective eyewear in accordance with claim 23 wherein said viewing apertures extend into said temple segments.

27. Protective eyewear in accordance with claim 15 wherein said nose piece additionally includes a nose bridge having nose pads at each end thereof.

28. Protective eyewear in accordance with claim 27 wherein said nose bridge and nose pads include means for cushioning blows transmitted from said nose piece to the nose of said wearer.

29. Protective eyewear in accordance with claim 28 wherein said cushioning means comprises a resilient protective liner attached to said nose bridge and nose pads and adapted to contact the nose of said wearer.

30. Protective eyewear in accordance with claim 15 additionally comprising means to secure said frame means to the head of said wearer.

31. Protective eyewear in accordance with claim 30 wherein said securing means comprises an elastic band attached between each of said temple members.

* * * * *

UNITED STATES PATENT AND TRADEMARK OFFICE
CERTIFICATE OF CORRECTION

PATENT NO. : 4,617,686

DATED : October 21, 1986

INVENTOR(S) : Arthur G. Nahas

It is certified that error appears in the above-identified patent and that said Letters Patent is hereby corrected as shown below:

Claim 1, line 28, the word "cross" should be the word --across--.

Signed and Sealed this

Tenth Day of February, 1987

*Attest:*

DONALD J. QUIGG

*Attesting Officer*   *Commissioner of Patents and Trademarks*